(12) United States Patent
Lessley et al.

(10) Patent No.: US 10,744,524 B2
(45) Date of Patent: Aug. 18, 2020

(54) VARIABLE VOLUME STRAND COATING APPARATUS AND METHOD

(71) Applicant: Illinois Tool Works Inc., Glenview, IL (US)

(72) Inventors: Mel Steven Lessley, Villa Hills, KY (US); Edward Wayne Bolyard, Jr., Old Hickory, TN (US)

(73) Assignee: Illinois Tool Works Inc., Glenview, IL (US)

( * ) Notice: Subject to any disclaimer, the term of this patent is extended or adjusted under 35 U.S.C. 154(b) by 0 days.

(21) Appl. No.: 16/100,992

(22) Filed: Aug. 10, 2018

(65) Prior Publication Data
US 2019/0047002 A1 Feb. 14, 2019

Related U.S. Application Data

(60) Provisional application No. 62/544,443, filed on Aug. 11, 2017.

(51) Int. Cl.
*B05B 9/04* (2006.01)
*B05C 5/02* (2006.01)
(Continued)

(52) U.S. Cl.
CPC ........ *B05B 9/0416* (2013.01); *A61F 13/4902* (2013.01); *B05C 5/0241* (2013.01);
(Continued)

(58) Field of Classification Search
CPC ... B05B 9/0416; B05C 5/0275; B05C 5/0225; B05C 11/10; B05C 11/1036; B05C 9/06;
(Continued)

(56) References Cited

U.S. PATENT DOCUMENTS

| 5,857,589 A | 1/1999 | Cline et al. |
| 6,688,498 B1 | 2/2004 | McGuffey |
| (Continued) | | |

FOREIGN PATENT DOCUMENTS

WO  2015053158 A1  4/2015

OTHER PUBLICATIONS

International Search Report and Written Opinion issued by ISA/EPO in connection with PCT/US2018/044916 dated Oct. 12, 2018.

*Primary Examiner* — Laura Edwards
(74) *Attorney, Agent, or Firm* — Levenfeld Pearlstein, LLC

(57) ABSTRACT

A fluid application device includes an applicator head, a first fluid passageway extending in the applicator head, a second fluid passageway extending in the applicator head, a plurality of metering devices connected to the applicator head. A first metering device of the plurality of metering devices is configured to meter a fluid to the first fluid passageway and a second metering device of the plurality of metering devices is configured to meter the fluid to the second fluid passageway. The device further includes a plurality of valve modules, each valve module actuatable between an open condition and a closed condition to control flow of the fluid and a nozzle having one or more discharge orifices. At least one orifice of the one or more discharge orifices is positioned downstream from the first passageway and the second passageway to receive the material from both the first and second fluid passageways.

8 Claims, 6 Drawing Sheets

(51) Int. Cl.
*B05C 9/06* (2006.01)
*B05C 11/10* (2006.01)
*A61F 13/49* (2006.01)
*B32B 37/12* (2006.01)
*A61F 13/15* (2006.01)

(52) U.S. Cl.
CPC .......... *B05C 5/0275* (2013.01); *B05C 5/0279* (2013.01); *B05C 9/06* (2013.01); *B05C 11/1036* (2013.01); *B32B 37/1292* (2013.01); *A61F 2013/1591* (2013.01); *A61F 2013/49025* (2013.01); *B05C 11/1005* (2013.01); *B32B 2555/02* (2013.01)

(58) Field of Classification Search
CPC . B05C 5/0241; B05C 5/0279; B05C 11/1005; B05C 5/004; B05C 5/00; B32B 37/1292; B32B 2555/02; A61F 13/4902; A61F 2013/49025; A61F 2013/1591
USPC .................................................. 118/300, 313
See application file for complete search history.

(56) References Cited

U.S. PATENT DOCUMENTS

| | | | |
|---|---|---|---|
| 8,413,848 B2 | 4/2013 | McGuffey | |
| 8,733,273 B2* | 5/2014 | Yamamoto | A61F 13/15739 118/314 |
| 2010/0230516 A1* | 9/2010 | Solie | B01F 5/0614 239/428 |
| 2011/0014369 A1* | 1/2011 | McGuffey | B05C 5/0225 427/207.1 |
| 2015/0128853 A1 | 5/2015 | Lessley et al. | |
| 2015/0128856 A1 | 5/2015 | Doyle et al. | |
| 2015/0273505 A1 | 10/2015 | Lessley | |
| 2016/0303597 A1 | 10/2016 | McGuffey | |
| 2017/0128968 A1 | 5/2017 | Adams et al. | |

* cited by examiner

VARIABLE VOLUME STRAND COATING APPARATUS AND METHOD

CROSS-REFERENCE TO RELATED APPLICATION DATA

This application claims the benefit of and priority to Provisional U.S. Patent Application Ser. No. 62/544,443, filed Aug. 11, 12018, titled, Variable Volume Strand Coating Apparatus and Method, the disclosure of which is incorporated herein in its entirety.

BACKGROUND

A strand coating system is configured to apply a hot melt adhesive onto one or more strands of material. Such a system is often used to coat elasticated strands of material with a hot melt adhesive for use in the construction of disposable hygiene products such as diapers. The coated elastic strands may be adhered to an underlying substrate with the hot melt adhesive to form, for example, leg elastics, cuff elastics or waist elastics of the disposable hygiene product.

The strand coating system includes a nozzle for discharging the hot melt adhesive onto the one or more elasticated strands of material. The nozzle assembly may be a contact applicator assembly for applying the adhesive directly onto the strands or a non-contact applicator assembly, where the adhesive is discharged over an air gap onto the strands. The nozzle includes an orifice through which the hot melt adhesive may be discharged. In one strand coating system, the flow of hot melt adhesive through the nozzle may be metered to control a coating weight of the hot melt adhesive on the strand of material.

In some applications, it may be desirable to vary a coating weight of the hot melt adhesive along a length of the strand of material. Such varied coating weights may be realized in a number of different ways. For example, the strand of material may be passed through a nozzle multiple times. For instance, a first pass through a nozzle may allow for a base coating on the strand, and a second or subsequent pass through the nozzle may allow for intermittent application of the hot melt adhesive to selectively add weight to the strand. However, such a process is time consuming and labor intensive.

Another system for varying the coating weight of a hot melt adhesive applied to the strand of material involves using two spaced apart nozzles arranged along a direction of travel of the strand of material. A first nozzle may apply a base coating of hot melt adhesive to the strand and a second nozzle may be controlled to add weight to the strand. However, such a system requires additional equipment (e.g., multiple nozzles) and may occupy a large area in a manufacturing assembly due to the additional equipment.

Still another system for varying a coating weight of a hot melt adhesive on a strand of material is described in U.S. Pat. Appl. Pub. No. 2017/0128968 to Adams et al., which is incorporated herein by reference in its entirety. In a non-contact application, Adams et al. uses two separate nozzles, independently operated, to apply the hot melt adhesive material to an elasticated strand. For example, one nozzle applies a base layer of hot melt adhesive to a plurality of elasticated strands, and a second, distinct nozzle is operated to apply a second layer of hot melt adhesive to the strands, thereby selectively adding weight to the strands. However, as described above, the use of multiple nozzles increases equipment and associated costs, maintenance, space and the like. In addition, by using a single nozzle and single orifice to apply the hot melt adhesive to multiple strands, overspray (discharged hot melt not received on a strand) may become an issue, which can lead to an inefficient coating process and increased material costs.

In a contact application, Adams et al. provides a nozzle having multiple discharge orifices arranged in a direction along a length of the elasticated strand. Flow of hot melt adhesive may be controlled through each discharge orifice as either on or off to control a coating weight of hot melt adhesive applied on the elasticated strand. That is, a coating weight of the hot melt adhesive may be controlled by allowing or preventing hot melt adhesive to be discharged from different discharge orifices. However, manufacture of such a nozzle requires significant machining, which may be time consuming and costly.

Accordingly, it is desirable to provide a fluid application device in a strand coating system capable of discharging varying volumes of a material from a single orifice of a nozzle.

SUMMARY

According to one aspect, a fluid application device includes a service an applicator head, a first fluid passageway extending in the applicator head, a second fluid passageway extending in the applicator head, and a plurality of metering devices connected to the applicator head. A first metering device of the plurality of metering devices is configured to meter a fluid to the first fluid passageway and a second metering device of the plurality of metering devices is configured to meter the fluid to the second fluid passageway. The fluid application device further includes a plurality of valve modules connected to the applicator head, each valve module actuatable between an open condition and a closed condition to control flow of the fluid, and a nozzle connected to the applicator head, the nozzle having one or more discharge orifices. At least one orifice of the one or more discharge orifices is positioned downstream from the first passageway and the second passageway and is configured to receive the material from each of the first and second fluid passageways.

According to another aspect, a method for varying a volume of material discharged from a nozzle orifice of a fluid application device includes metering a first volume of material to the nozzle orifice via a first fluid passageway, metering a second volume of material to the nozzle orifice via a second fluid passageway, and controlling flow of the second volume of material to the nozzle orifice with a valve module in the second fluid passageway. Controlling flow of the second volume of material includes opening the valve module to provide the second material to the nozzle orifice, and closing the valve module to prevent flow of the second material to the nozzle orifice.

Other objects, features, and advantages of the disclosure will be apparent from the following description, taken in conjunction with the accompanying sheets of drawings, wherein like numerals refer to like parts, elements, components, steps, and processes.

DETAILED DESCRIPTION

Figure 1:
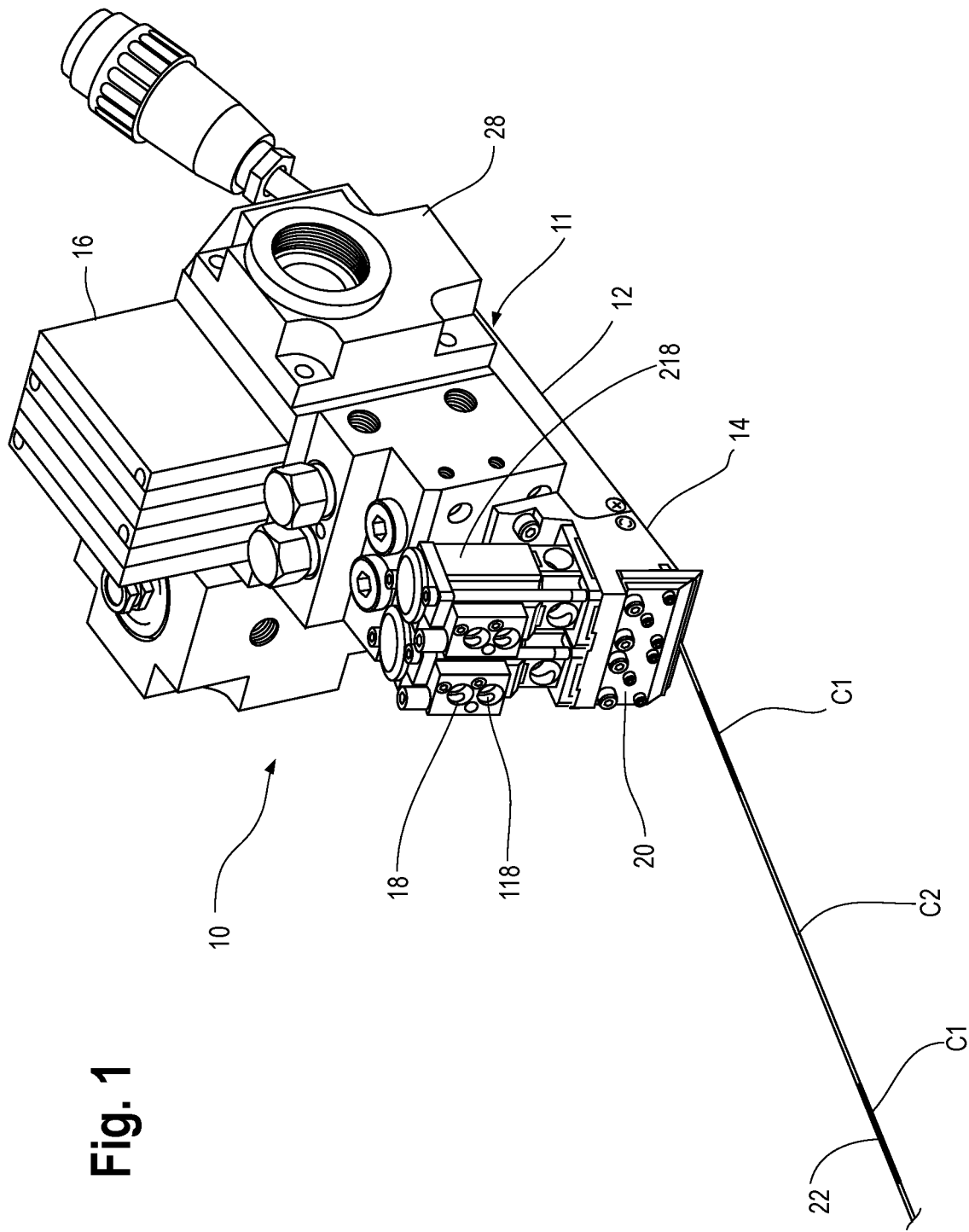
FIG. 1 is a perspective view of a fluid application device according to an embodiment described herein.

While the present disclosure is susceptible of embodiment in various forms, there is shown in the drawings and will hereinafter be described one or more embodiments with the understanding that the present disclosure is to be considered illustrative only and is not intended to limit the disclosure to any specific embodiment described or illustrated.

Figure 2:
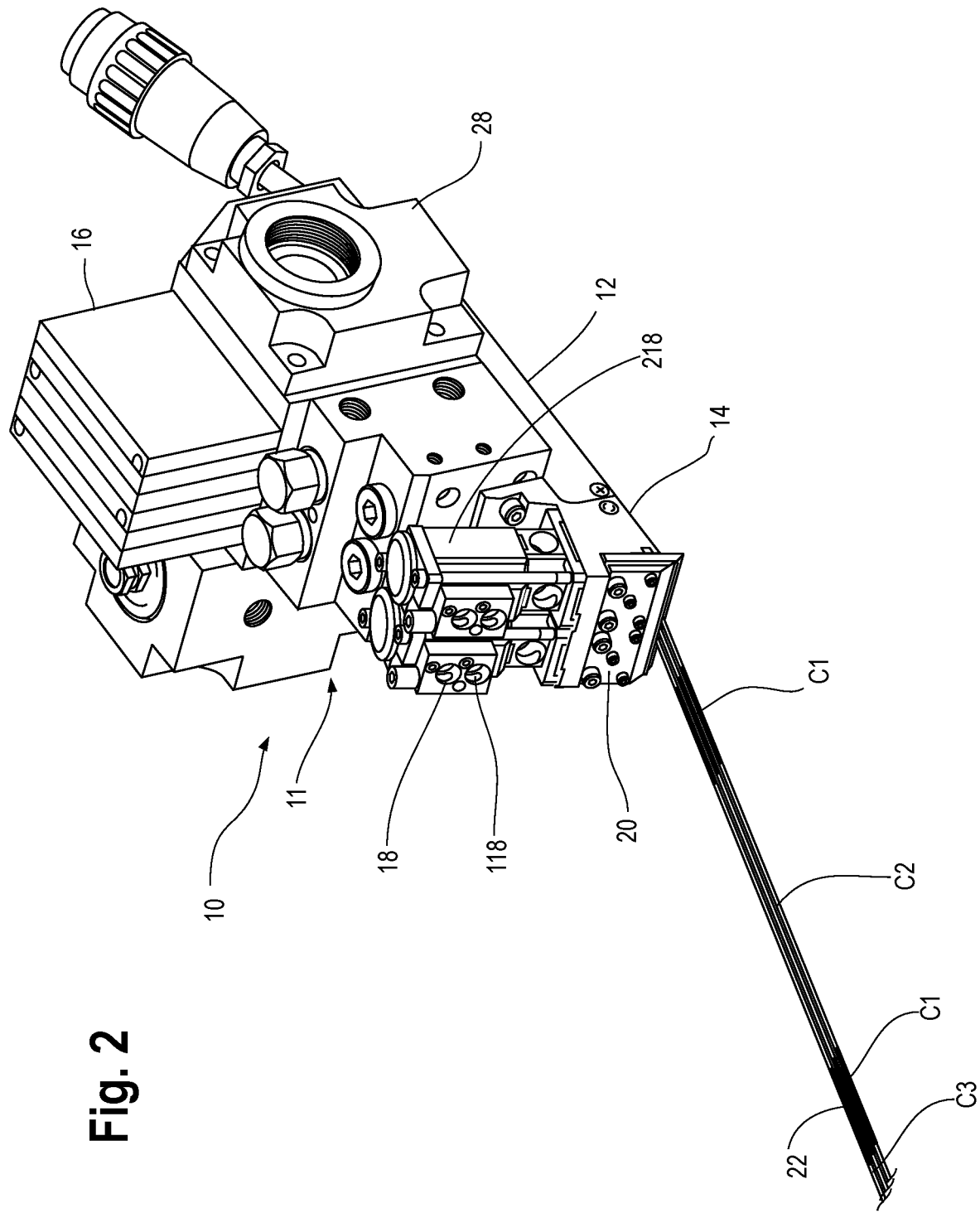
FIG. 2 is a perspective view of a fluid application device according to another embodiment described herein.

FIG. 1 is a perspective view of a fluid application device 10 according to an embodiment described herein. FIG. 2 is a perspective view of a fluid application device 10 according to another embodiment. Referring to FIGS. 1 and 2, the fluid application device 10 includes, generally, an applicator head 11, a plurality of metering devices 16, one or more valve modules 18 and a nozzle 20. The applicator head 11 may include, for example, a service block 12 and an adapter 14 secured to one another. In one example, the service block 12 and adapter may be secured directly to one another in an abutting relationship. In one embodiment, the nozzle 20 is a contact applicator configured to apply a material onto individual strands 22. In another embodiment, the nozzle 20 may be a non-contact applicator or a slot die applicator. In a contact applicator or nozzle, material is applied directly onto strands or a substrate. That is, the strand or substrate is in contact or near contact with the material or an orifice from which the material is discharged, as the material is discharged. In a non-contact applicator or nozzle, the material is discharged over an air gap onto the strand or substrate. First and second fluid passageways 24, 26 (see FIGS. 4 and 5) are formed in the applicator head 11, for example, in the the service block 12 and adapter 14, to allow flow of the material through the service block 12 and the adapter 14 to the nozzle 20.

In one embodiment, the plurality of metering devices 16 may be one or more pumps. In one embodiment, the pumps may be gear pumps. The gear pumps may be provided in the form of a plurality of stacked plates having gears driven by a common motor. In some embodiments, the gear pumps may be those shown and disclosed in U.S. Pat. App. Pub. No. 2016/0303597 to McGuffey, commonly owned with the present application, and incorporated herein by reference in its entirety, or those shown and disclosed in U.S. Pat. No. 6,688,498 to McGuffey or U.S. Pat. No. 8,413,848 to McGuffey, both of which are commonly owned with the present application and incorporated herein by reference in their entireties. The metering devices 16 may be mounted or removably mounted directly to the applicator head 11, for example, to the service block 12. In another embodiment, the metering devices 16 may be remotely positioned from the applicator head 11.

Figure 4:
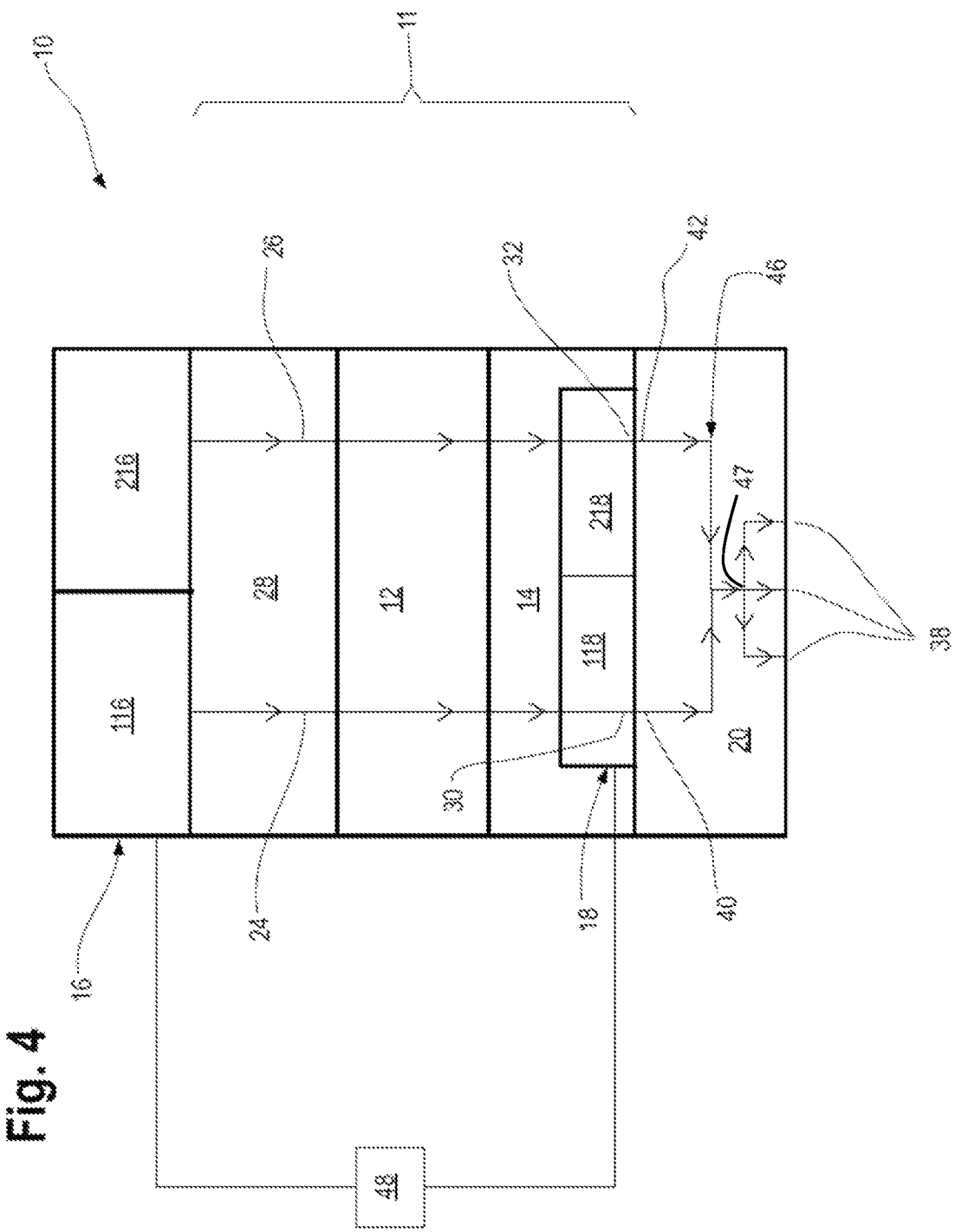
FIG. 4 is a schematic diagram showing fluid flow paths according to an embodiment described herein.
Figure 5:
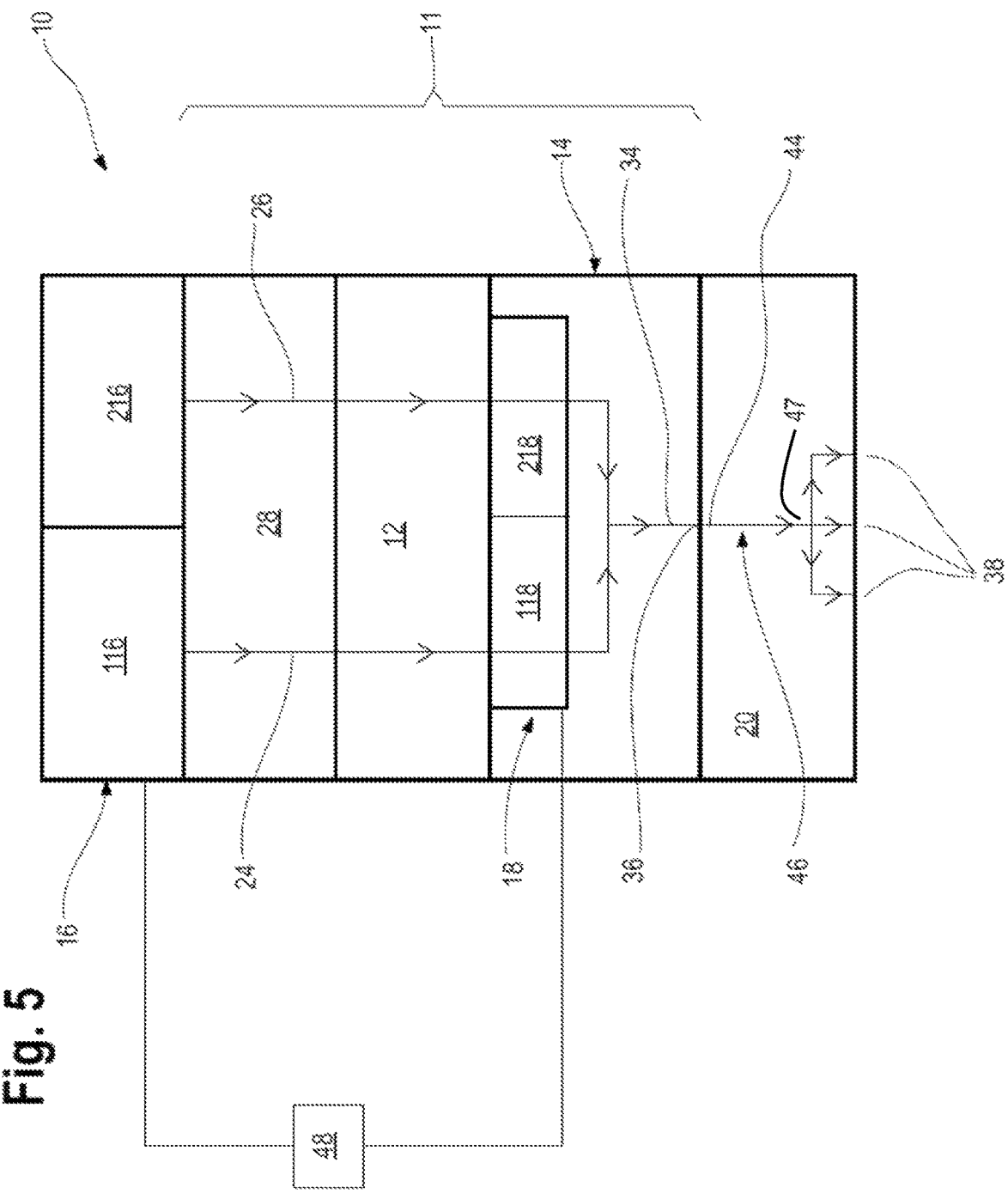
FIG. 5 is a schematic diagram showing fluid flow paths according to another embodiment described herein.

The metering devices 16 are configured to receive a material, such as a hot melt adhesive, from a supply source (not shown). Referring to FIGS. 4 and 5, in one embodiment, the metering devices 16 include a first metering device 116 configured to meter the material to the first fluid supply passageway 24 and a second metering device 216 configured to meter the material to the second fluid supply passageway 26. That is, the first metering device 116 is configured to meter a first portion or volume of the material and the second metering device 216 is configured to meter a second portion or volume of the material. In one embodiment, the applicator head 11 may further include a manifold 28 disposed between the metering devices 16 and the service block 12, and the metering devices 16 may be removably mounted directly to the manifold 28. The first and second fluid passageways 24, 26 extend through the manifold 28.

The adapter 14 is connected to the service block 12 using known, suitable fasteners, such as threaded fasteners and the like, and is fluidically connected to the service block 12 to receive the material from the first and second fluid passageways 24, 26. Referring to FIG. 4, in one embodiment, the first and second fluid passageways 24, 26 extend through the adapter 14 to respective first and second outlets 30, 32.

Referring to FIG. 5, in another embodiment, the first and second fluid passageways 24, 26 may intersect to form a third fluid passageway 34 in the applicator head 11, for example in the adapter 14 or service block 12. The third fluid passageway 34 extends to a single material outlet 36.

The nozzle 20 is secured to the applicator head 11, for example, to the adapter 14, using known suitable fasteners, such as a threaded fastener and the like. The nozzle 20 is fluidically connected to the adapter 14 and is configured to receive the material from the adapter 14. In one embodiment, the nozzle 20 includes one or more discharge orifices 38 to discharge the material. In one embodiment, the nozzle 20 includes first and second inlets 40, 42 configured to receive the material from the first and second outlets 30, 32, respectively, of the adapter 14. In another embodiment, the nozzle 20 include a single material inlet 44 configured to receive the material from the single material outlet 36 corresponding to the third fluid passageway 34 of the adapter 14. The one or more discharge orifices 38 are positioned downstream from the first fluid passageway 24 and the second fluid passageway 26 and are configured to selectively receive and discharge the material from both the first and second fluid passageways 24, 26.

As shown in FIG. 4, the nozzle 20 includes one or more internal conduits 46 interconnected between the first and second fluid passageways 24, 26 and the one or more discharge orifices 38. The one or more internal conduits 46 may intersect such that material received in the nozzle 20 from the first and second fluid passageways 24, 26 may be combined into a single flow. The one or more internal conduits may also include a splitting section 47 down stream from the intersection where the flow of material may be split for discharge from a plurality of orifices 38. In another embodiment, as shown in FIG. 5, the material may be received in the nozzle 20 from the third fluid passageway 34, and split among a plurality of discharge orifices 38 by the internal conduits 46.

In one embodiment, the nozzle 20 may be a laminated plate nozzle comprising a plurality of stacked plates secured together with suitable fasteners, such as threaded fasteners. Examples of such laminated nozzle plates are shown and described in U.S. Pat. App. Pub. No. 2015/0128856 to Lessley et al., commonly owned with the present application and incorporated herein by reference in its entirety. In one embodiment, the plurality of discharge orifices 38 may be disposed along a common line. For example, the discharge orifices 38 may all be disposed on a single plate of the stacked plates. However, the present disclosure is not limited to such a configuration.

As shown in FIGS. 1-5, the one or more valve modules 18 may include a first valve module 118 and a second valve module 218. The first valve module 118 includes a first valve configured to actuate between an open condition and a closed condition in the first fluid passageway 24. In the open condition, material flow is permitted through the first fluid passageway 24 and in the closed condition, material flow is limited or prevented. Similarly, the second valve module 218 includes a second valve configured to actuate between an open condition and a closed condition in the second fluid passageway 26. In the open condition, material flow is permitted through the second fluid passageway 26 and in the closed condition, material flow is limited or prevented. The one or more valve modules 18 may be mounted on the adapter 14 or the service block 12. The first and second valves may be solenoid valves but are not limited thereto.

Figure 3:
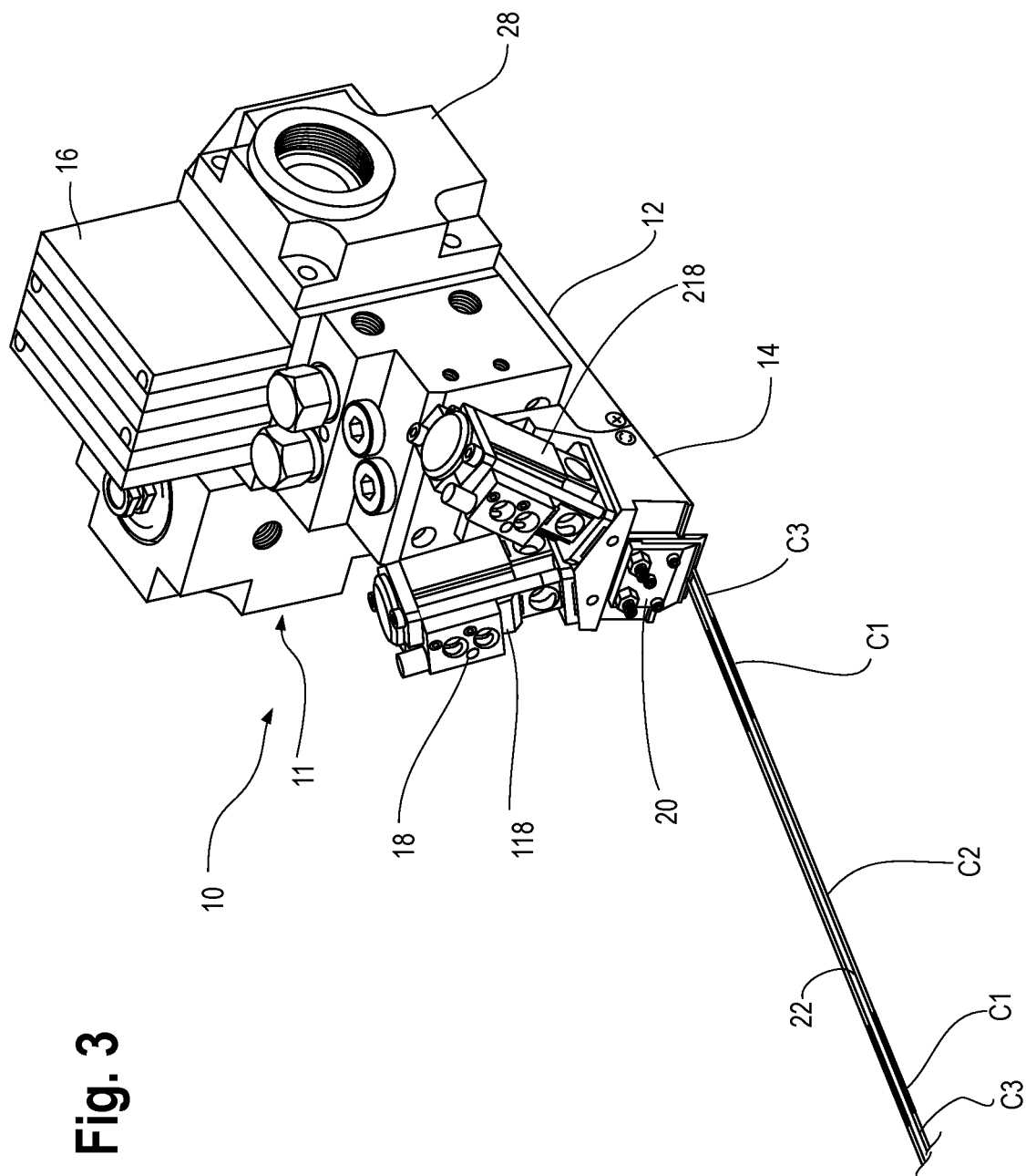
FIG. 3 is a perspective view of another fluid application device according to another embodiment described herein.

Referring to FIG. 3, in one embodiment, the first and the second valve modules 118, 218 may be mounted on the applicator head 11 at a non-parallel angle relative to one another. In such a configuration, the applicator head, for example, at the adapter 14, may include angled faces on which the valve modules 118, 218 are mounted. Alternatively, the valve modules 118, 218 may include angled mounting faces. Corresponding valves of the valve modules 118, 218 project along lines which intersect. Accordingly, when projected to a closed position, the valves of the valve modules 118, 128 move toward one another and are laterally closer to one another in the closed condition than in the open condition. Accordingly, the first and second fluid passageways 24, 26 may be positioned closer to one another. Because of a shorter distance between the first and second fluid passageways 24, 26, a nozzle 20 having a smaller width may be used.

The fluid application device may further include a controller 48 operatively connected to the valve modules 118, 218. The controller 48 is configured control actuation of the valves between open and closed condition. For example, the controller 48 may actuate the valves at predetermined intervals or in response to operator input. In addition, the controller 48 may be operatively connected to the metering device 16 to control flow rate through the first and second metering devices 116, 216, for example. In one embodiment, the controller 48 may be connected to a drive motor of the metering device 16 to control an output of the drive motor.

The fluid application device may include additional components such as, but not limited to, a heater, a filter, power inputs, and strand positioning elements for positioning strands of material relative to the nozzle 20. Further, as shown in FIGS. 1-3, varying numbers of strands 22 may be fed by the nozzle 20. For example, as shown in FIG. 1, a single strand 22 is fed by the nozzle 20. In FIG. 2, three strands 22 are fed by the nozzle 20, and in FIG. 3 two strands 22 are fed by nozzle 20. The present disclosure is not limited to such numbers of strands 22, however. In one embodiment, each discharge orifice 38 discharges the material onto a respective strand 22.

In the embodiments above, the first metering device 116 meters a first volume of material to the first fluid passageway 24. The first volume of material subsequently flows into the third fluid passageway 34 or the internal conduits 46 of the nozzle 20. The first volume of fluid then flows to one or more of the discharge orifices 38 to be discharged and applied to one or more respective strands 22. The second metering device 216 meters a second volume of material to the second fluid passageway 26. The second volume of material subsequently flows into the third fluid passageway 34 or the internal conduits 46 of the nozzle 20. The second volume of fluid then flows to one or more of the discharge orifices 38 to be discharged and applied to one or more respective strands 22, such that the first volume of material and second volume of material are discharged together from the same orifice 38 or orifices 38. The second volume of material may be the same as or different from the first volume of material.

Discharge of the first and second volumes of material may be controlled by the valve module 18. In one embodiment, the valve module 18 includes the first valve module 118 and the second valve module 218, which are selectively disposed in the first and second fluid passageways 24, 26, respectively. In an open condition, the valve modules 118, 218 allow for passage of the first and second volumes of material, respectively, and in a closed condition, the first and second valve modules 118, 218 prevent flow of the first and second volumes of material, respectively.

In use, the nozzle 20, and in particular, an orifice 38 of the nozzle 20, may discharge the first volume of material to apply a first coating weight of the material on the one or more strands 22. The second volume of material may be discharged from the same orifice 38, together with the first volume of material, to provide an add-on or increased coating weight of the material to the one or more strands 22. A controller 48 may be operable connected to the valve modules 118, 218 to control opening and closing of the valve modules 118, 218. Accordingly, as a strand 22 is fed by the nozzle 20 of the fluid application device 10, a coating weight of the material applied on the strand may be varied by controlling the first and second valve modules 118, 218.

The fluid application device 10 is operable in a number of different states based on the condition of the first and second valve modules 118, 218. In a first state, the first valve module 118 is open and the second valve module 218 is closed. Accordingly, a first volume of material may be discharged from the orifices(s) 38 to apply a first coating weight on the strand(s). In a second operating state, the first valve module 118 and the second valve module 218 are open. Accordingly, a first volume and a second volume of the material are simultaneously discharged from the orifice(s) to apply a second coating weight on the strand(s). In a third operating state, both the first valve module 118 and second valve module 218 are closed, such that no material, or substantially no material is discharged from orifice(s) or applied to the strand(s). In a fourth state, the first valve module 118 may be closed and the second valve module 218 may be opened, such that only the second volume of material is discharged from the orifice(s) to a apply a third coating weight on the strand(s). Referring to FIGS. 1-3, the strands 22 may include lengths having different coating weights. For example, a first coating weight is shown at C1, a second coating weight at C2, and an uncoated section at C3. The present disclosure is not limited to such coating weights or patterns, however.

Figure 6:
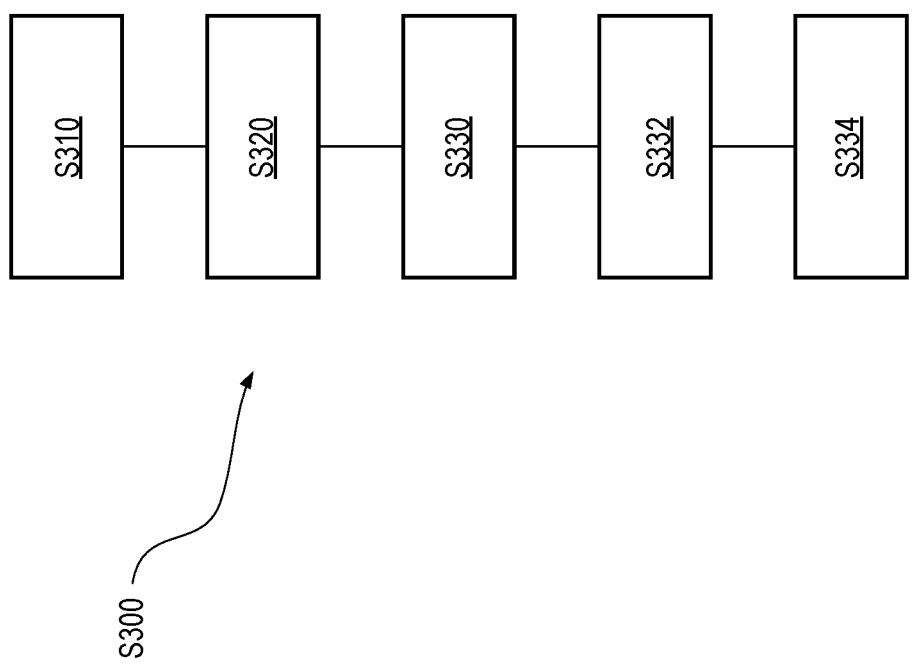
FIG. 6 is a diagram showing a method of varying a volume of material discharged from a nozzle orifice in the fluid application device, according to one embodiment.

FIG. 6 is a diagram showing a method S300 of varying a volume of material discharged from a nozzle orifice of a fluid application device. According to the embodiments described herein, the method includes metering a first volume of material to a first fluid passageway 24 at S310, metering a second volume of material to a second fluid passageway 26 at S320, and controlling flow of the second volume of material to the nozzle orifice 38 with a valve module 218 in the second fluid passageway at S330. Controlling flow of the second volume of material includes opening the valve module 218 to provide the second material to the nozzle orifice at S332, and closing the valve module 218 to prevent flow of the second material to the nozzle orifice 38 at S334. The nozzle orifice 38 includes a plurality of nozzle orifices 38. The method may further include controlling flow of the first volume of material by opening or closing another valve module 118 to selectively allow or prevent flow of the first volume of material to the orifice 38.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

The invention claimed is:

1. A fluid application device comprising:
an applicator head;
a first fluid passageway extending in the applicator head;
a second fluid passageway extending in the applicator head; the applicator head comprising a service block and an adapter, the first and second fluid passageways extend in the service block and the adapter;
a plurality of pumps connected to the applicator head, a first pump of the plurality of pumps configured to meter a fluid to the first fluid passageway and a second pump of the plurality of pumps configured to meter the fluid to the second fluid passageway, the first fluid passageway configured to receive the fluid from first pump and the second fluid passageway configured to receive the fluid from the second pump;
a plurality of valve modules connected to the applicator head, each valve module actuatable between an open condition and a closed condition to control flow of the fluid in the first fluid passageway and the second fluid passageway; and
a nozzle fluidically connected to the applicator head and configured to receive the fluid from the first fluid passageway and the second fluid passageway, the nozzle having a plurality of discharge orifices, wherein at least one orifice of the plurality of discharge orifices is positioned downstream from the first passageway and the second passageway,
wherein the nozzle includes an internal conduit fluidically connected between the first and second fluid passageways and the plurality of discharge orifices for receiving the fluid from the first and second fluid passageways, and the internal conduit includes a splitting section to split the fluid for flow to the plurality of discharge orifices, and
wherein the plurality of orifices are disposed along a common line.

2. The fluid application device of claim 1, wherein the plurality of valve modules includes a first valve module configured to control flow of the fluid in the first fluid passageway.

3. The fluid application device of claim 2, wherein the plurality of valve modules includes a second valve module configured to control flow of the fluid in the second fluid passageway.

4. The fluid application device of claim 3, wherein the valve modules are operable to provide:
a first operating condition in which the first valve module is open and the second valve module is closed such that a first volume of the fluid is received by the nozzle and discharged from the at least one orifice; and
a second operating condition in which the first valve module is open and the second valve module is open such a second volume of the fluid is received by the nozzle and discharged from the at least one orifice.

5. The fluid application device of claim 1, wherein the first fluid passageway and second fluid passageway intersect to form a third fluid passageway, and the third fluid passageway is fluidically connected to an inlet of the nozzle and the internal conduit.

6. The fluid application device of claim 1, wherein the first fluid passageway is fluidically connected to a first inlet of the nozzle and the second fluid passageway is fluidically connected to a second inlet of the nozzle, and the first inlet and the second inlet are fluidically connected to the internal conduit.

7. The fluid application device of claim 1, wherein each discharge orifice of the plurality of discharge orifices is fluidically connected to the first fluid passageway and the second fluid passageway.

8. The fluid application device of claim 1, wherein the applicator head further comprises a manifold disposed between the plurality of pumps and the service block, and the first and second fluid passageways extend through the manifold.

* * * * *